(12) United States Patent
Klimovitch et al.

(10) Patent No.: US 7,993,338 B2
(45) Date of Patent: Aug. 9, 2011

(54) SWITCHING METHODS AND APPARATUS

(75) Inventors: Gleb V. Klimovitch, Santa Clara, CA (US); Timothy E. Ciciarelli, San Jose, CA (US); Shena H. Park, San Francisco, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1226 days.

(21) Appl. No.: 11/700,074

(22) Filed: Jan. 31, 2007

(65) Prior Publication Data
US 2008/0183169 A1    Jul. 31, 2008

(51) Int. Cl.
*A61B 18/04* (2006.01)
(52) U.S. Cl. ................. 606/42; 606/32; 606/34
(58) Field of Classification Search .............. 606/32–35, 606/41–42
See application file for complete search history.

(56) References Cited

U.S. PATENT DOCUMENTS

| | | |
|---|---|---|
| 5,056,517 A | 10/1991 | Fenici |
| 5,170,139 A | 12/1992 | Nelson |
| 5,230,349 A | 7/1993 | Langberg |
| 5,298,817 A | 3/1994 | Banak et al. |
| 5,348,554 A | 9/1994 | Imran et al. |
| 5,423,811 A | 6/1995 | Imran et al. |
| 5,462,521 A | 10/1995 | Brucker et al. |
| 5,545,161 A | 8/1996 | Imran |
| 5,643,197 A | 7/1997 | Brucker et al. |
| 5,792,140 A | 8/1998 | Tu et al. |
| 5,843,152 A | 12/1998 | Tu et al. |
| 5,888,198 A | 3/1999 | Eggers |
| 5,913,856 A | 6/1999 | Chia et al. |
| 6,017,338 A | 1/2000 | Brucker et al. |
| 6,161,543 A | 12/2000 | Cox et al. |
| 6,212,426 B1 * | 4/2001 | Swanson ............... 600/510 |
| 6,237,605 B1 | 5/2001 | Vaska et al. |
| 6,311,692 B1 | 11/2001 | Vaska et al. |
| 6,552,626 B2 | 4/2003 | Sharpe et al. |
| 6,602,242 B1 | 8/2003 | Fung et al. |

(Continued)

OTHER PUBLICATIONS

F. Wittkampf et al., "Radiofrequency Ablation With a Cooled Porous Electrode Catheter," JACC, vol. 11, No. 2, Feb. 1988:17A Abstracts.

(Continued)

*Primary Examiner* — Linda C Dvorak
*Assistant Examiner* — Amanda Scott
(74) *Attorney, Agent, or Firm* — Dykema Gossett PLLC

(57) ABSTRACT

Embodiments of the invention controlling power distribution in an ablation control apparatus or the like. In one embodiment, a power switching apparatus comprises a first switch assembly having an input end to receive a power input signal, the first switch assembly having a plurality of output channels; a second switch assembly coupled to the output channels of the first switch assembly; a plurality of power receiving members coupled to the second switch assembly; and a controller controlling the first switch assembly to selectively transmit the power input signal to the output channels one at a time in a cyclical manner according to a first switching rate. The controller controls the second switch assembly to transmit the power input signal from the output channels of the first switch assembly to one subset of the power receiving members at a time according to a second switching rate, so as to transmit the power input signal to a subset of power receiving members one power receiving member at a time within the subset of power receiving members according to the first switching rate.

18 Claims, 11 Drawing Sheets

U.S. PATENT DOCUMENTS

| | | |
|---|---|---|
| 6,611,699 B2 | 8/2003 | Messing |
| 6,689,128 B2 | 2/2004 | Sliwa, Jr. et al. |
| 6,719,755 B2 | 4/2004 | Sliwa, Jr. et al. |
| 7,166,105 B2 | 1/2007 | Mulier et al. |
| 2004/0254570 A1* | 12/2004 | Hadjicostis et al. ............ 606/27 |

OTHER PUBLICATIONS

International Search Report and Written Opinion filed in PCT/US2008/052648, mailed Jul. 8, 2008.

* cited by examiner

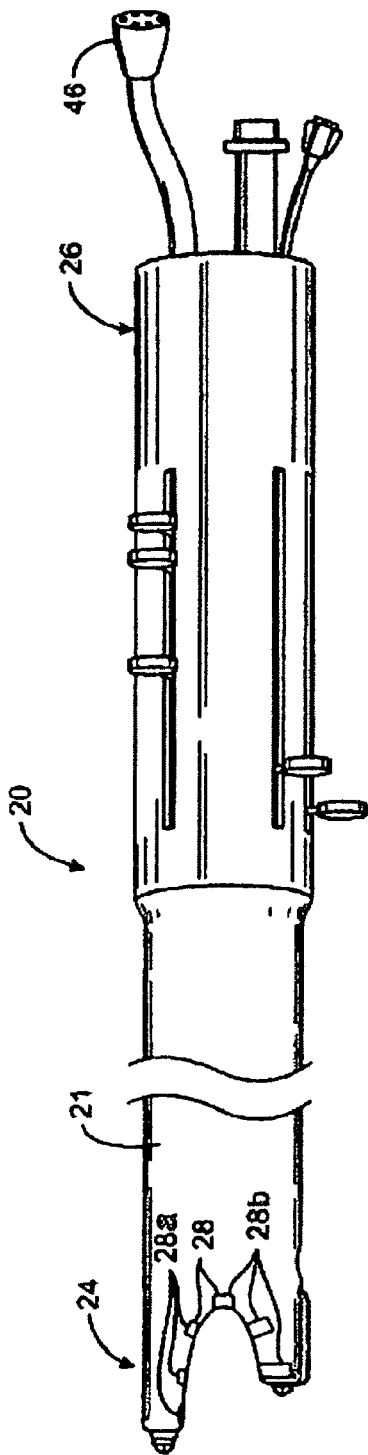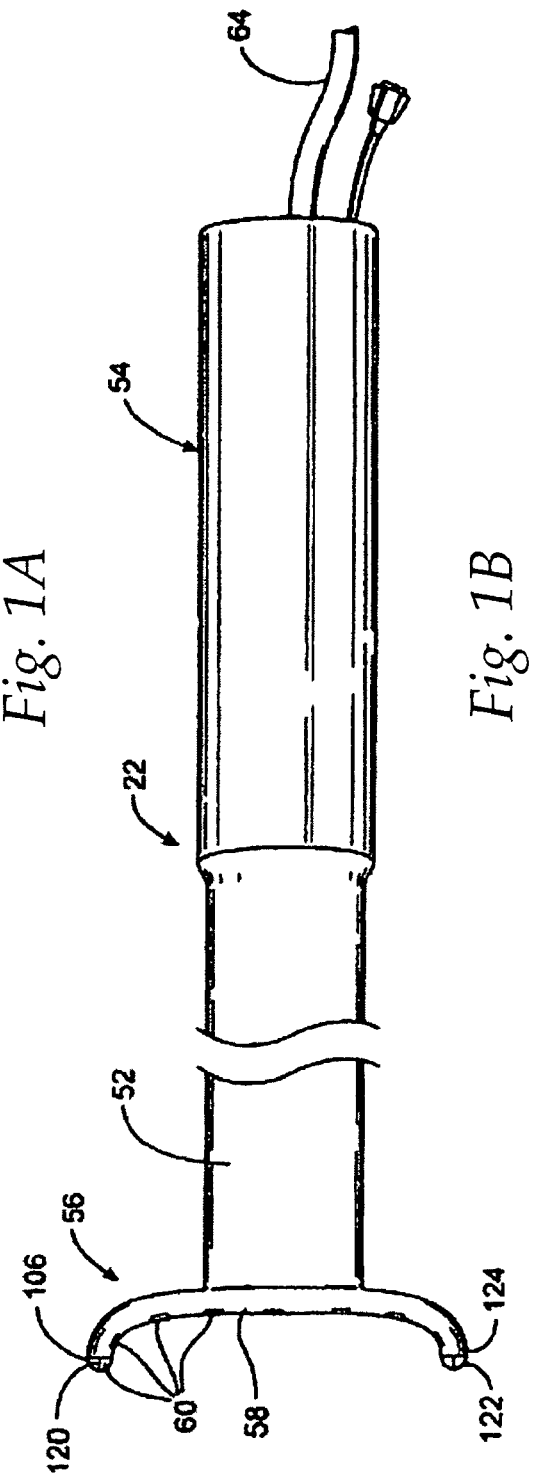
Fig. 1A
Fig. 1B

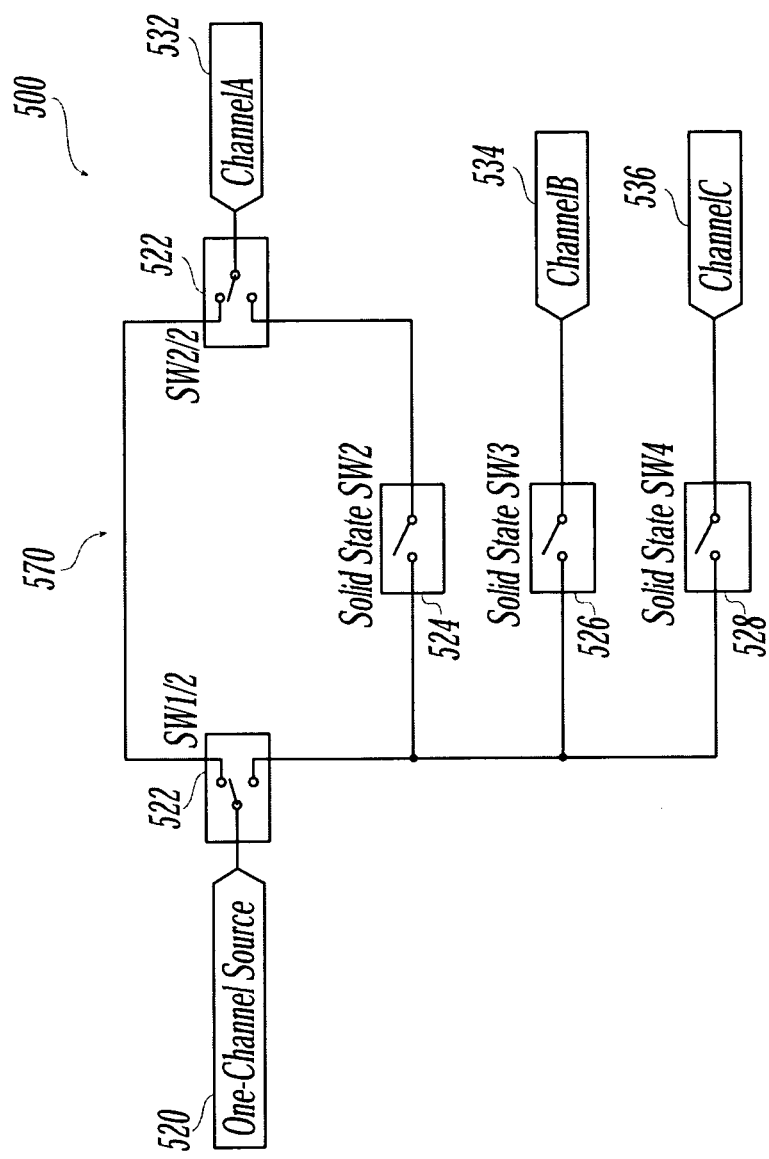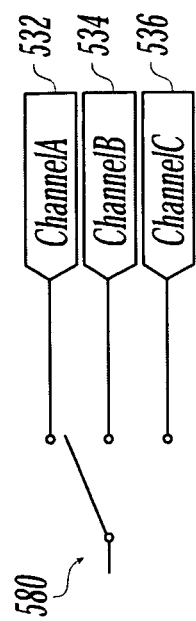
Fig. 9
Fig. 9A

SWITCHING METHODS AND APPARATUS

FIELD OF THE INVENTION

The instant invention relates to power switching apparatus and methods that may be used for controlling power distribution in an ablation control apparatus.

BACKGROUND OF THE INVENTION

The pumping action of the heart is controlled by electrical stimulation of myocardial tissue. Stimulation of this tissue in various regions of the heart is controlled by a series of conduction pathways contained within the myocardial tissue.

Cardiac arrhythmias arise when the pattern of the heartbeat is changed by abnormal impulse initiation or conduction in the myocardial tissue. The term tachycardia is used to describe an excessively rapid heartbeat resulting from repetitive stimulation of the heart muscle. Such disturbances often arise from additional conduction pathways which are present within the heart either from a congenital developmental abnormality or an acquired abnormality which changes the structure of the cardiac tissue, such as a myocardial infarction.

One of the ways to treat such disturbances is to identify the conductive pathways and to sever part of this pathway by destroying these cells which make up a portion of the pathway. Traditionally, this has been done by either cutting the pathway surgically; freezing the tissue, thus destroying the cellular membranes; or by heating the cells, thus denaturing the cellular proteins. The resulting destruction of the cells eliminates their electrical conductivity, thus destroying, or ablating, a certain portion of the pathway. By eliminating a portion of the pathway, the pathway may no longer maintain the ability to conduct, and the tachycardia ceases.

One of the most common ways to destroy tissue by heating has been the use of electromagnetic energy. Typically, ablating elements emit radiofrequency (RF), microwave, ultrasound, and/or laser energy to destroy tissue. With RF energy, a catheter with a conductive inner core and a metallic tip are placed in contact with the myocardium and a circuit is completed with a patch placed on the patient's body behind the heart. The catheter is coupled to an RF generator such that application of electrical energy creates localized heating in the tissue adjacent to the distal (emitting) electrode. The peak tissue temperatures during catheter delivered application of RF energy to the myocardium occur close to the endocardial surface, such that the lesion size produced is limited by the thermodynamics of radiant heat spread from the tip. The amount of heating which occurs is dependent on the area of contact between the electrode and the tissue and the impedance between the electrode and the tissue. The higher the impedance, the lower the amount of energy transferred into the tissue. For ultrasonic ablation, the amount of heating may depend on the energy of the signal, the focal length of the transducer delivering the energy, the frequency of the energy, and/or the duration that the energy is applied to the tissue to be ablated.

Power may be delivered to the ablating elements through channels, with one channel per power source. In embodiments with less than one power source per channel, where each channel does not have its own power source, power would have to be switched between channels fast enough so that the rate of tissue ablation decreases insignificantly. The time it takes the rate of tissue ablation to decrease insignificantly is known as the thermal time constant. The switching cycle must be at least as fast as the thermal time constant. One switching cycle is defined as the time it takes to circulate power among all channels for one full cycle. If an AC power source is used, this produces modulated pulse train power signals in the channels. If there were one power source supplying power to M channels with a thermal time constant T, power would have to switch from one channel to the next in T/M seconds.

While a solid state switching matrix can be used to increase switching speed, such a matrix would generate electrical parasitics which would result in unacceptable signal distortion. Signal distortion can be a change in signal power at the operating frequency, and it can be a harmonic distortion (i.e. the ratio of the signal power at a frequency other than the operating frequency to the signal power at the operating frequency). During operation, solid state switches can produce distortions of up to a 15% change in signal power, and/or a total harmonic distortion of up to 5%. However, during calibration of an ablating device, these distortions should be less than approximately 0.25% (for either form of distortion). A need therefore exists for an apparatus that reduces the number of power sources required without generating unacceptable levels of signal distortion.

BRIEF SUMMARY OF THE INVENTION

The instant invention relates to power switching apparatus and methods that may be used for controlling power distribution in an ablation control apparatus. In specific embodiments, two layers of switching mechanisms are used to quasi-simultaneously distribute power to a plurality of power receiving members such as ablation elements. The first layer of switching mechanism performs fast switching of the power input signal that is sufficiently fast to distribute power among multiple ablation elements so that the rate of tissue ablation remains substantially constant. The second layer of switching mechanism directs the power input signal to the plurality of ablation elements one subset at a time, so that the ablation elements within the subset perform ablation at the substantially constant rate of tissue ablation. The switching speed of the second layer of switching mechanism is substantially lower than the switching speed of the first layer of switching. For fast switching, more durable solid state switches are typically used in the first layer of switching mechanism. For slower switching, electro-mechanical relays may be used.

In accordance with an aspect of the present invention, a power switching apparatus comprises a plurality of first switches having an input end to receive a power input signal, each first switch having an output end; a plurality of second switches, each second switch having an input end coupled to the output end of at least one first switch, each second switch having an output end; a plurality of power receiving members, each power receiving member having an input end coupled to the output end of at least one second switch; and a controller selectively turning on the first switches one at a time in a cyclical manner according to a first switching rate to transmit the power input signal, the controller selectively turning on the second switches one subset of the second switches at a time according to a second switch rate to transmit the power input signal from the first switches to a subset of power receiving members one power receiving member at a time within the subset of power receiving members according to the first switching rate. The first switching rate is substantially faster than the second switching rate.

In specific embodiments, the first switching rate is faster than the second switching rate by at least one order of magnitude. Each subset of the second switches are equal in number to the first switches and equal in number to each subset of the power receiving members. The first switches are solid state switches. The second switches are electromechanical relays. The power receiving members are arranged in a closed loop, and wherein each subset of the power receiving members forms a group of neighboring power receiving members within a portion of the closed loop. The first switching rate is such that for each first switching cycle, a first switching period is at most about 0.1 seconds and the first switches are each turned on once for about the same duty cycle over the first switching period. Three first switches may be provided. There may be N power receiving members, M first switches, and at most M×N second switches. Alternatively, there may be N power receiving members, M first switches, and at most M+N second switches. The apparatus may further comprise a bypass switch having an input end to receive the power input signal and an output end coupled to the second switches. In an on position, the bypass switch bypasses the first switches to transmit the power input signal to the second switches. When the bypass switch is in the on position, the controller selectively turns on the second switches to transmit the power input signal to the power receiving members one at a time in a cyclical manner.

In accordance with another aspect of the invention, a power switching apparatus comprises a plurality of first switches having an input end to receive a power input signal, each first switch having an output end; a plurality of second switches, each second switch having an input end coupled to the output end of at least one first switch, each second switch having an output end; a plurality of ablation members, each ablation member having an input end coupled to the output end of at least one second switch; and a controller selectively turning on the first switches one at a time in a cyclical manner according to a first switching rate to transmit the power input signal, the controller selectively turning on the second switches one subset of the second switches at a time according to a second switch rate to transmit the power input signal from the first switches to a subset of ablation members one ablation member at a time within the subset of ablation members according to the first switching rate. The first switching rate is such that for each first switching cycle, a first switching period is at most about T seconds during which each first switch is turned on once, and that a rate of tissue ablation of the tissue to be ablated by each ablation member remains substantially constant during the first switching period.

In specific embodiments, the first switching rate is such that the rate of tissue ablation of the tissue to be ablated by each ablation member changes at most by about 5% during the first switching period. The first switching period may be at most about 0.1 seconds.

In accordance with another aspect of the invention, a power switching apparatus comprises a plurality of first switches having an input end to receive a power input signal, each first switch having an output end; a plurality of second switches, each second switch having an input end coupled to the output end of at least one first switch, each second switch having an output end; and a plurality of power receiving members, each power receiving member having an input end coupled to the output end of at least one second switch. The first switches are configured to be selectively turned on one at a time in a cyclical manner according to a first switching rate to transmit the power input signal one at a time. The second switches are configured to be selectively turned on one subset at a time according to a second switch rate to transmit the power input signal from the first switches to one subset of power receiving members one power receiving member at a time within the subset of power receiving members according to the first switching rate. The first switches are substantially more durable than the second switches when operated at a switching rate such that a switch is turned on and off at least once every 0.1 seconds.

In specific embodiments, the first switches are at least 10 times more durable, more preferably at least 100 times more durable, than the second switches when operated at a switching rate such that a switch is turned on and off at least once every 0.1 seconds.

In accordance with another aspect of the invention, a power switching apparatus comprises a plurality of first switches having an input end to receive a power input signal, each first switch having an output end; a plurality of power receiving members; and a mechanism for selectively turning on the first switches one at a time in a cyclical manner according to a first switching rate to transmit the power input signal, to one subset of power receiving members at a time according to a second switch rate, so as to transmit the power input signal from the first switches to a subset of power receiving members one power receiving member at a time within the subset of power receiving members according to the first switching rate.

In accordance with another aspect of the invention, a power switching method comprises supplying a power input signal to a plurality of first switches; and selectively turning on the first switches one at a time in a cyclical manner according to a first switching rate to transmit the power input signal, to one subset of a plurality of power receiving members at a time according to a second switch rate, so as to transmit the power input signal from the first switches to a subset of power receiving members one power receiving member at a time within the subset of power receiving members according to the first switching rate. In specific embodiments, the method further comprises bypassing the first switches to transmit the power input signal to the power receiving members one at a time in a cyclical manner.

In accordance with another aspect of the present invention, a power switching apparatus comprises a first switch assembly having an input end to receive a power input signal, the first switch assembly having a plurality of output channels; a second switch assembly coupled to the output channels of the first switch assembly; a plurality of power receiving members coupled to the second switch assembly; and a controller controlling the first switch assembly to selectively transmit the power input signal to the output channels one at a time in a cyclical manner according to a first switching rate, the controller controlling the second switch assembly to transmit the power input signal from the output channels of the first switch assembly to one subset of the power receiving members at a time according to a second switching rate, so as to transmit the power input signal to a subset of power receiving members one power receiving member at a time within the subset of power receiving members according to the first switching rate.

In specific embodiments, the output channels of the first switch assembly are equal in number to each subset of the power receiving members. The first switching rate is substantially faster than the second switching rate. The power receiving members are ablation members. The first switching rate is such that for each first switching cycle, a first switching period is at most about T seconds during which each first switch is turned on once, and that a rate of tissue ablation of the tissue to be ablated by each ablation member remains substantially constant during the first switching period.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1A is side view of a left ablation probe.

FIG. 1B is a side view of a right ablation probe.

FIG. 9 illustrates an embodiment of an ablation control system with four terminal sets.

FIG. 9A illustrates a single-pole triple-throw (SPTT) switch in an alternative embodiment of switching in the ablation control system of FIG. 9.

DETAILED DESCRIPTION OF THE INVENTION

Figure 2:
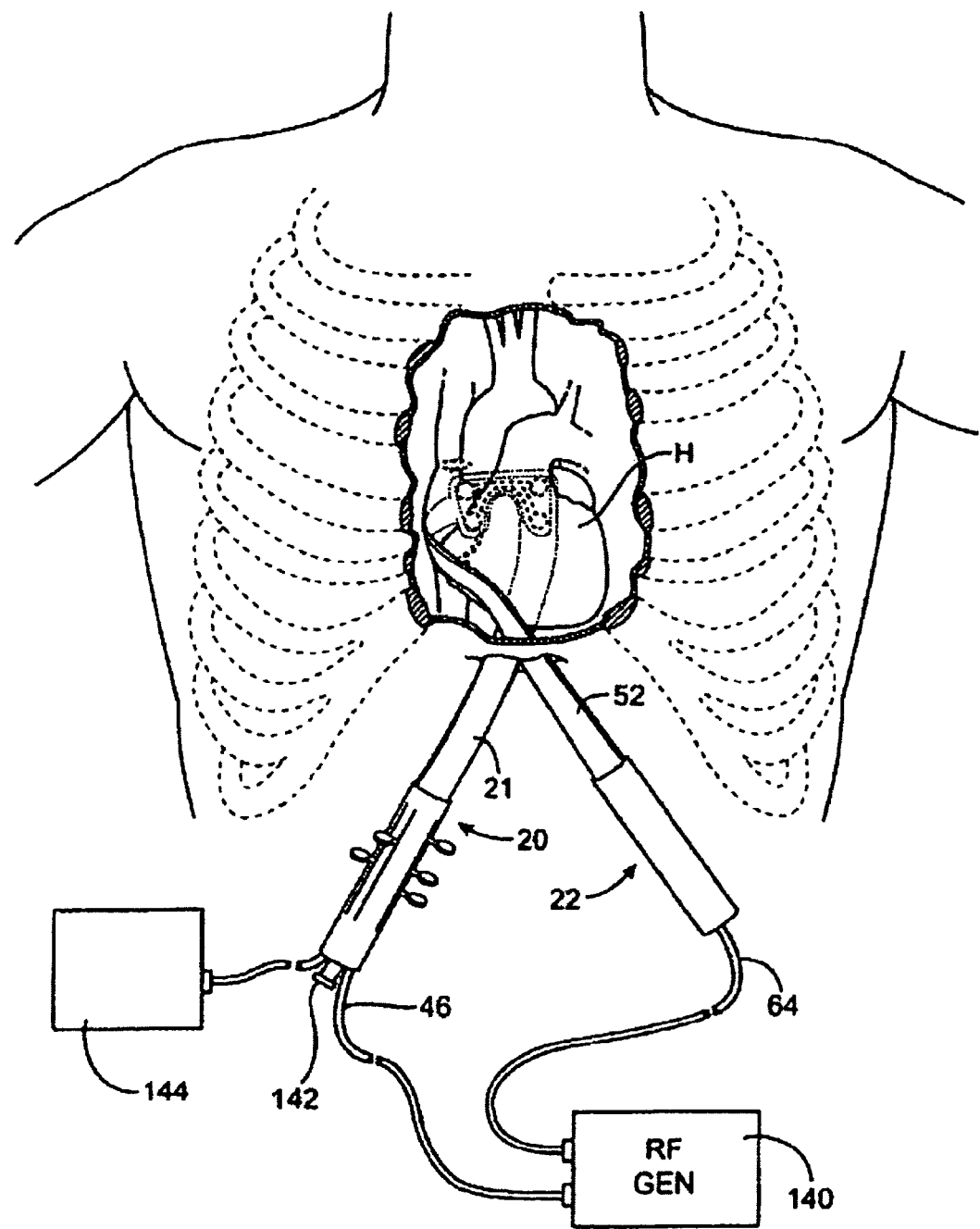
FIG. 2 illustrates an embodiment of the left and right ablation probes inserted in a chest cavity.

FIGS. 1A and 1B illustrate an embodiment of an ablation control system with a left and right ablation probe 20, 22. FIG. 1A is side view of the left ablation probe 20, and FIG. 1B is a side view of a right ablation probe 22. The two probes work in tandem to form a transmural lesion isolating the pulmonary veins from the surrounding myocardium. The left ablation probe 20 has a flexible shaft 21 extending to a working end 24 configured for insertion into the chest cavity through a small incision, puncture or access port. Opposite working end 24, shaft 21 is attached to a control end 26 used for manipulating the working end 24 from outside the chest. Shaft 21 is dimensioned to allow introduction through a small incision in the chest, preferably in a subxiphoid location, and advanced to the pulmonary veins on the posterior side of the heart. Preferably, shaft 21 is configured to be flexible about a first transverse axis to allow anterior-posterior bending and torsional flexibility, but relatively stiff about a second transverse axis perpendicular to the first transverse axis to provide lateral bending stiffness. In an exemplary embodiment, shaft 21 has a length in the range of about 10-30 cm, and a guide portion having a rectangular cross-section with a width-to-height ratio of about 2:5, the cross-sectional width being about 6-35 mm and the cross-sectional height being about 3-17 mm. The guide portion aligns the device between the epicardium and pericardium to ablate tissues as described below. The shaft 21 is made of a flexible biocompatible polymer such as polyurethane or silicone, and preferably includes radiopaque markers or a radiopaque filler such as bismuth or barium sulfate. The right ablation probe 22 has a flexible shaft 52 extending from a control end 54 to a working end 56. Working end 56 has a cross-member 58 to which are mounted a plurality of electrodes 60. Cross member 58 preferably has tips 106, 124 which are pre-shaped or deflectable into a curve so as to conform to the right lateral walls of the right pulmonary veins, and which are separated by a distance selected so that the two right pulmonary veins may be positioned between them, usually a distance of about 20-50 mm.

Each ablation probe 20, 22 has at least one ablating element for forming lesions. Each ablating element has at least one radiofrequency (RF) electrode. The RF electrode is item 28 in FIG. 1A and item 60 in FIG. 1B. In the embodiment shown in FIG. 1A, the at least one electrode 28 delivers RF current to the myocardium to create transmural lesions of sufficient depth to block electrical conduction. At least one electrical connector 46 provides power to the at least one RF electrode 28. A catheter with a conductive inner core and a metallic tip may be placed in contact with the myocardium, and a circuit is completed with a patch placed on the patient's body behind the heart. The catheter is coupled to an RF generator such that application of electrical energy creates localized heating in the tissue adjacent to the distal (emitting) electrode. The at least one electrode 28 may contain partially-insulated solid metal rings or cylinders, foil strips, wire coils or other suitable construction for producing elongated lesions. Electrodes 28 are spaced apart a distance selected so that the lesions created by adjacent electrodes contact or overlap one another, thereby creating a continuous, uninterrupted lesion in the tissue underlying the at least one electrode 28. In the embodiment in FIG. 1B, electrodes 60 are about 2-20 mm in length and spaced approximately 1-6 mm apart. Each electrode 60 is sized and positioned to create a continuous lesion along the right side (from the patient's perspective) of the pulmonary veins. At least one electrical connector 64 provides power to the at least one RF electrode 60. As an alternative to the RF electrodes 28, 60 in FIGS. 1A and 1B the at least one ablating element 27 may have at least one microwave transmitter, cryogenic element, laser, heated element, ultrasound, hot fluid and/or any other element suitable for forming transmural lesions.

Figure 3:
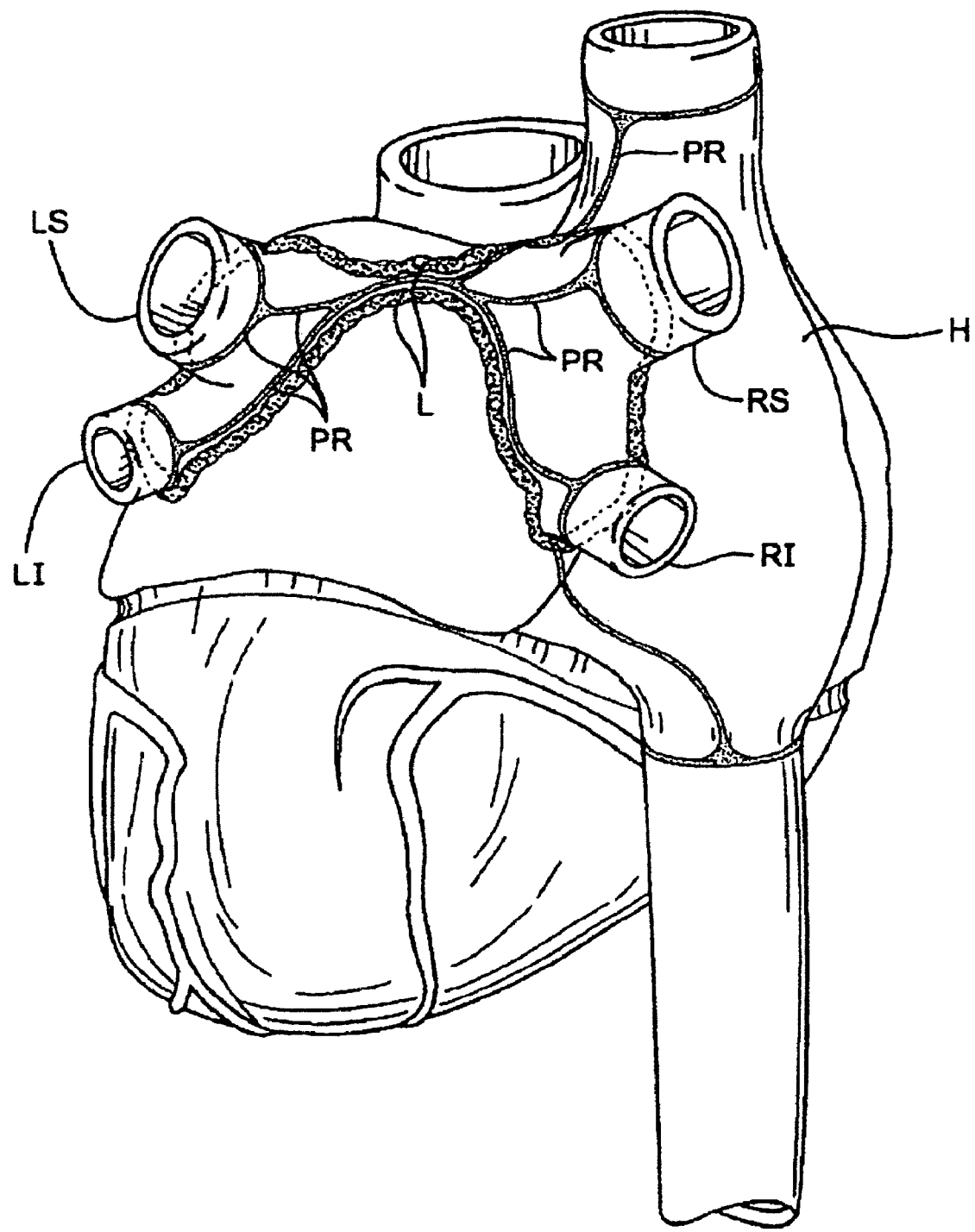
FIG. 3 illustrates a transmural lesion formed by the left and right ablation probes.

FIG. 2 illustrates the left and right ablation probes 20, 22 inserted in a chest cavity. FIG. 3 shows a transmural lesion formed by the left and right ablation probes 20, 22. In the embodiment shown, left ablation probe 20 and right ablation probe 22 are connected to an RF generator 140. The RF generator 140 preferably provides up to 150 watts of power at about 500 kHz, and can preferably monitor both temperature and impedance. A suitable generator would be, for example, a model number EPT-1000 available from the EP Technologies Division of Boston Scientific Corporation of Natick, Mass. Retraction, visualization, temperature monitoring, suction, irrigation, mapping or ablation devices may be inserted through working port 142. The left ablation probe 20 may further be connected to a source of suction or inflation fluid 144. If electromagnets are provided on left and right ablation probes 20, 22 an additional connection may be made to a power supply and switch for operating the electromagnets, or power may be supplied by RF generator 140 through connectors 46, 64. The RF generator 140 is then activated to deliver RF energy to electrodes 28, 60 on left and right ablation probes 20, 22 producing the transmural lesion L shown in FIG. 3. Preferably, power in the range of 20-150 watts is delivered at a frequency of about 500 kHz for about 30-180 seconds, resulting in localized myocardial temperatures in the range of 45-95 degrees C. Ultrasound visualization may be used to detect the length, location and/or depth of the lesion created. Lesion L forms a continuous electrically-insulated boundary encircling the pulmonary veins thereby electrically isolating the pulmonary veins from the myocardium outside of lesion L.

Figure 4:
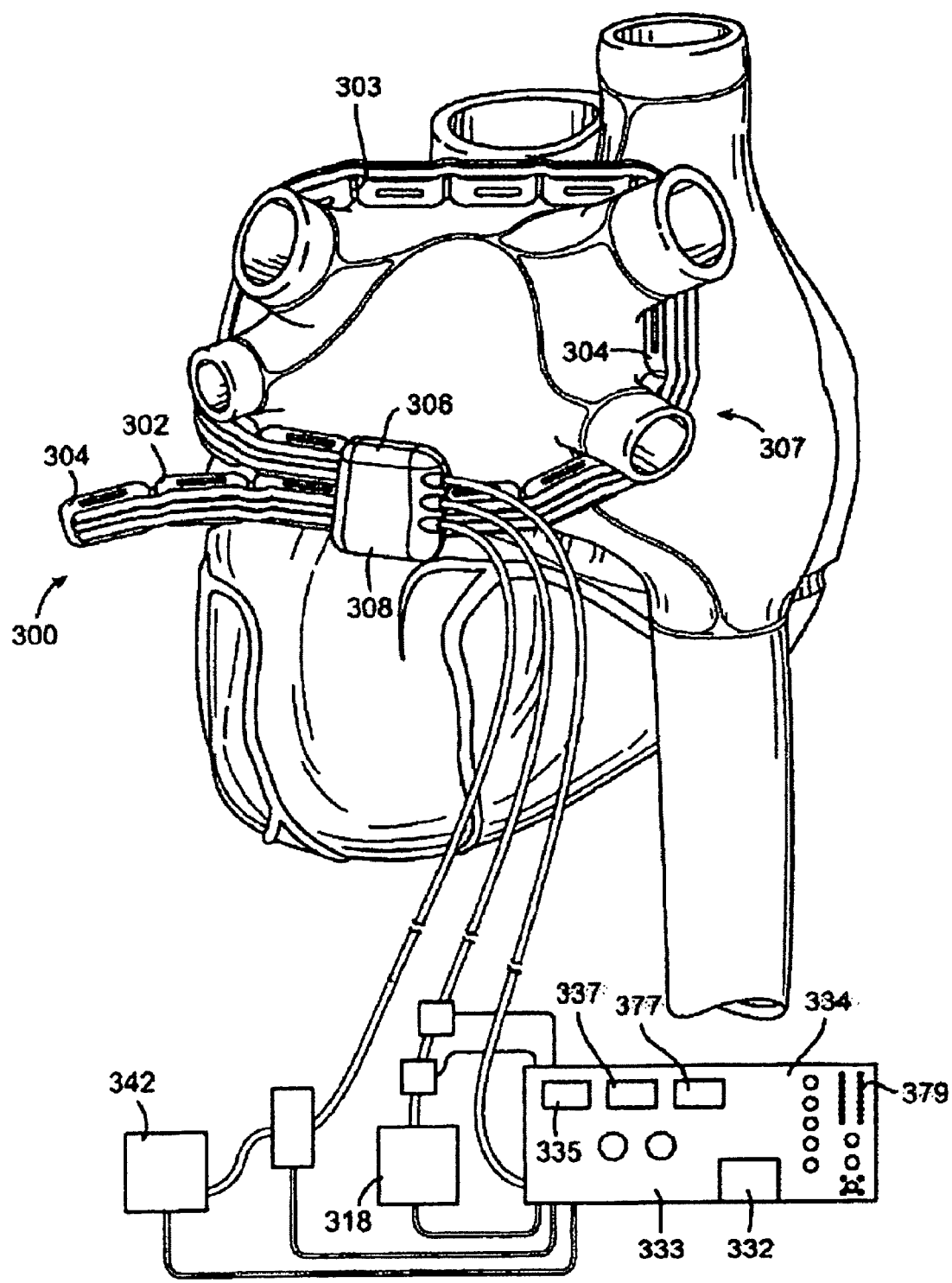
FIG. 4 illustrates another embodiment of an ablation device.

FIG. 4 illustrates another embodiment of a device 300 for ablating tissue. The device contains at least one ablating element 311 (see FIG. 5) for forming lesions. The device 300 may also be used in any manner described herein and may have the features and dimensions of other devices described herein without departing from the scope of the invention. The device 300 encircles the pulmonary veins and is particularly suited for conventional open chest surgery but may also be used in less and minimally invasive procedures. Although ablation of tissue around the pulmonary veins is described as a specific use of the device 300, the device 300 may be used on other parts of the heart and in other areas of the body. The device 300 has a body 302 having a length of 5-12 inches, preferably about 10 inches, and a width of 0.2-0.7 inch preferably about 0.5 inch. The body 302 is preferably made of a polymeric material such as silicone or urethane and is formed by injection molding although any suitable material and method may be used to form the body 302. The body 302 has a number of cells 304 coupled together by integrally formed hinges 303 in the body 302. Of course, the cells 304 may be coupled together with mechanical connections rather than the integrally formed hinges 303 without departing from the scope of the invention. The ablating device 300 preferably has 5-30 cells 304, more preferably 10-25 cells 304, and most preferably about 16 cells 304, although any number of cells 304 may be used depending upon the specific application. For example, the ablating device 300 may be used to extend around a single vessel, such as the aorta, pulmonary vein, SVC or IVC in which case the ablating device 300 has 4-12 cells 304, preferably about eight cells 304. The device 300 has a locking mechanism 306, preferably a buckle 308, which engages another part of the device 300 to form a closed loop 307. The device 300 extends around the pulmonary veins with the locking mechanism 306 to form the closed loop 307 around the pulmonary veins. Although a buckle 308 is preferred, the locking mechanism 306 may have any other suitable structure for locking one part of the device 300 to another part of the device 300.

Figure 5:
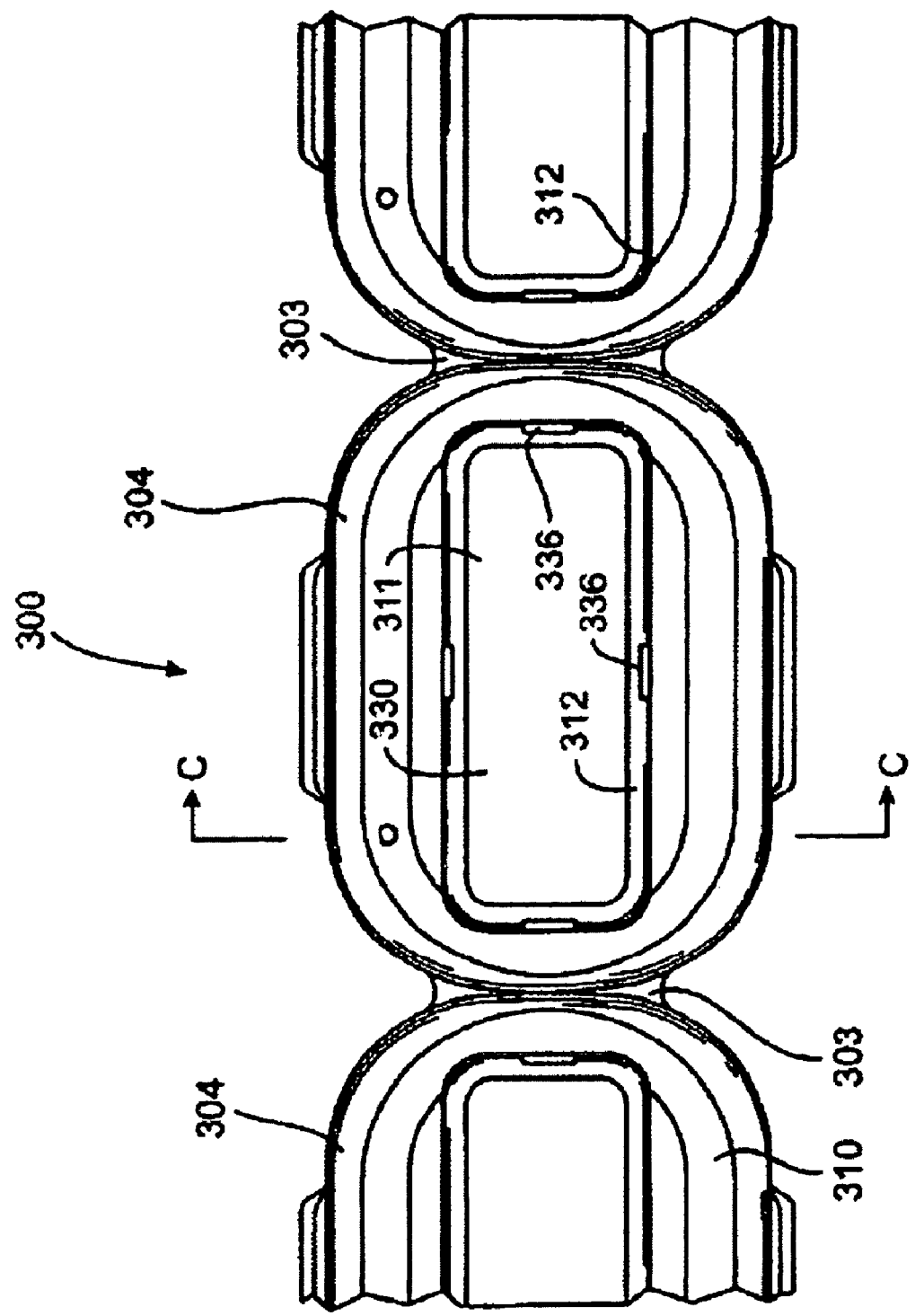
FIG. 5 illustrates an embodiment of an RF ablating element.

FIG. 5 illustrates an embodiment of an RF ablating element 311. The ablating element 311 may be contained in the ablating device 300 shown in FIG. 4. Although an RF ablating element 311 is shown, the ablating element 311 may be any ablating element mentioned herein. In the embodiment shown, the ablating element 311 is located in a cell 304 of the ablating device 300. The RF electrode 330 is coupled to an RF generator 332 (shown in FIG. 4) which transmits RF energy to the electrode. The RF generator 332 provides up to 150 watts of power at about 500 kHz, preferably in the range of 20-150 watts at a frequency of about 500 kHz, for about 30-180 seconds. It also preferably monitors both temperature and impedance. The RF electrode 330 is preferably a stainless steel or gold plated copper electrode, although any suitable conductive material may be used. The ablating element 311 preferably has a width of 1-6 mm, preferably about 3 mm, and a length of 2-25 mm, preferably about 12 mm. When the ablating element 311 is the RF electrode, the ablating element 311 is preferably spaced apart from the target tissue, or from a bottom of the inner lip 312, by a distance of 0.5-3 mm and more preferably about 1.5 mm. The locking mechanism 306 preferably has at least one ablating element 311 to create a continuous lesion in tissue beneath the locking mechanism 306.

Figure 6:
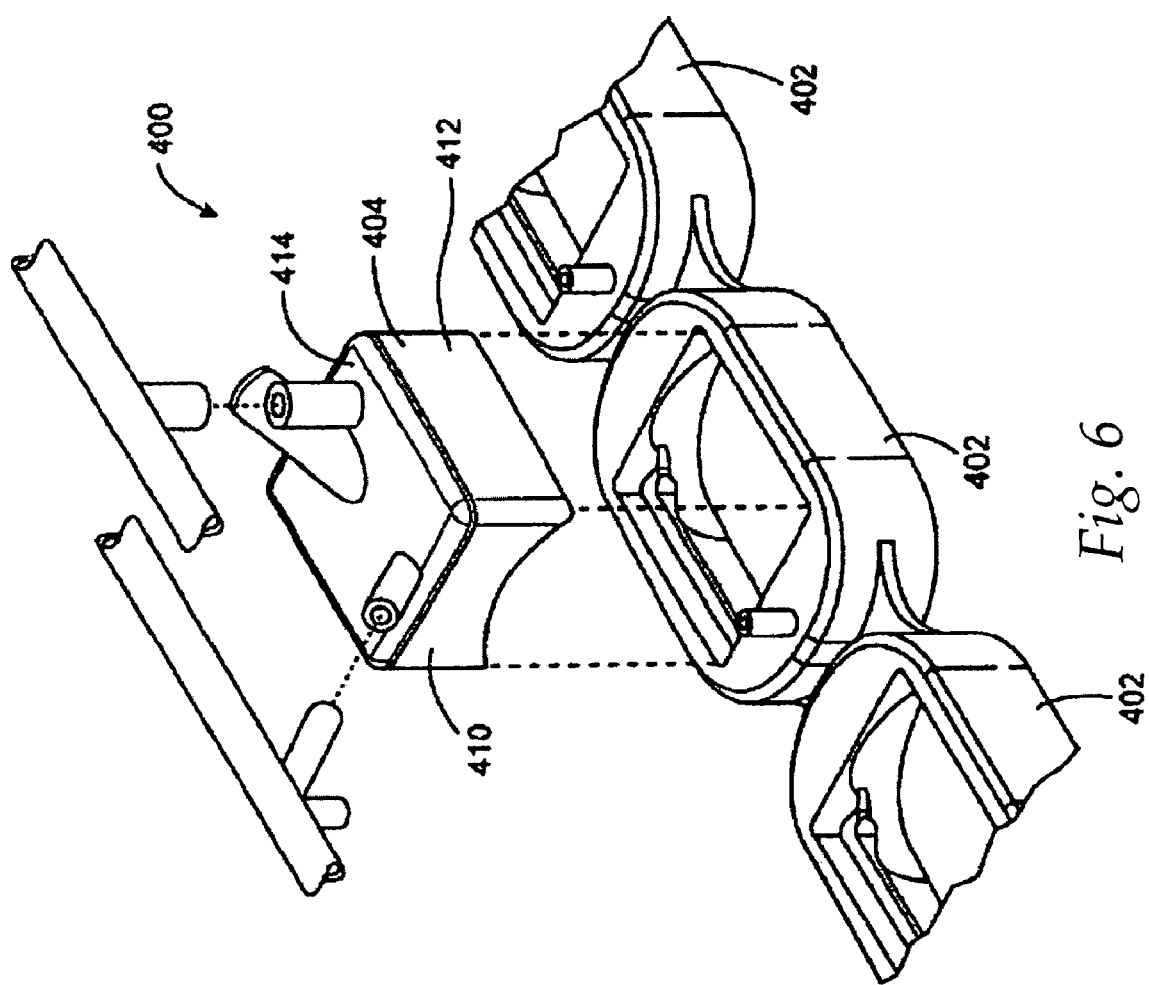
FIG. 6 illustrates an embodiment of an ultrasonic ablating element.
Figure 7:
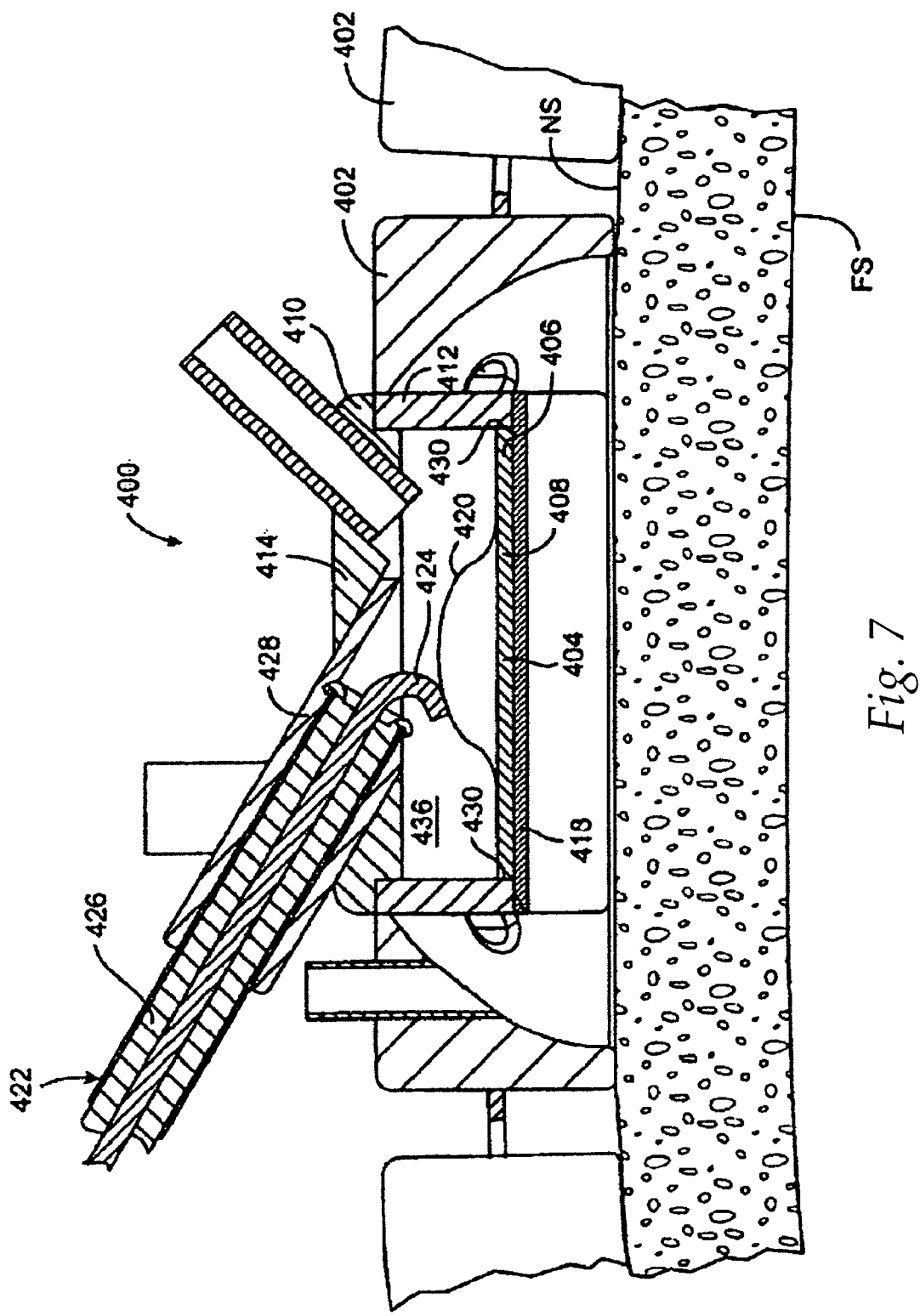
FIG. 7 is a cross-sectional view of an embodiment of an ultrasonic ablating element.

Other types of ablating elements may be used with or in place of RF electrodes. The ablating elements may have at least one RF transmitter, microwave transmitter, ultrasound transmitter, cryogenic element, laser, heated element, hot fluid, or other types of ablation device suitable for forming transmural lesions. The ablating elements 404 may also be designed to operate at different frequencies and/or powers. FIGS. 6 and 7 illustrate an embodiment of an ablating element with an ultrasonic transducer 406. An advantage of using focused ultrasonic energy is that the energy can be concentrated within the tissue. The at least one ultrasonic transducer 406 is contained in at least one ablating element 404 in at least one cell 402 (shown in FIG. 6). The ultrasonic transducer 406 is preferably a piezoelectric element 408. The energy may also be produced by a number of transducers (not shown) which are oriented to focus or concentrate ultrasonic energy. For example, a multielement acoustic phased array (not shown) may be used to provide an acoustic beam-steering capability from the at least one ablating element 404. One skilled in the art can also appreciate the use of multiple matching layers (not shown), focusing acoustic lenses (not shown) and non-focusing acoustic windows (not shown). Although the embodiment of the ablating device 400 illustrated in FIGS. 6 and 7 has an ultrasonic transducer 406, other embodiments may use any other type of ablating element 404, and may be combined with any of the features in other embodiments. Thus, the at least one ablating element 404 may produce focused energy in a number of different ways, including ways not mentioned here, without departing from the scope of the invention.

In the embodiment shown in FIG. 7, a distributing element 420 is attached to the transducer 406 at two locations to distribute energy that drives the transducer 406. The distributing element 420 is preferably a piece of copper ribbon 0.020 inch wide and 0.0005 inch thick soldered to the transducer 406 at two locations. A coaxial cable 422 delivers power to the transducer 406 from a source of power (not shown) and provides a ground path. The coaxial cable 422 has a power lead 424 coupled to the distributing element 420 to power the transducer 406. A braided portion 426 of the cable 422 serves as a ground. The braided portion 426 is soldered to a tube 428 and/or the top 414. The ground path leads from the transducer 406 to a layer 418 which is preferably made of aluminum but may be made of other suitable material, and then to a housing 410. The ground path then passes to the top 414 and finally to the braided portion 426 either directly or via the tube 428. The tube 428 and top 414 are preferably made of brass and the enclosure 412 is preferably made of aluminum, although any other suitable materials may be used. Polyimide tape 430 is adhered to the inside of the enclosure 412 and on the transducer 406 to electrically separate the two structures.

Ablating devices may be controlled by a controller 334 (shown in FIG. 4). The ablating element 311 is electrically coupled to the controller 334 with at least one wire (not shown). The controller 334 may be connected in series, or in parallel to the ablating elements 311. In another embodiment, the ablating elements 311 may be contained in a switching matrix (not shown). The switching matrix may also be connected to the controller by one or more wires (not shown) which may be in series or in parallel. Other means of connecting the controller 334 to the ablating element 311 may be used as long as the controller 334 is in electrical communication with the ablating elements 311. The controller 334 controls distribution of power between ablating elements. The controller 334 causes the ablating device 300 to ablate tissue by controlling the power delivered to the tissue by the at least one ablating element 311. The controller 334 may deliver power to ablating elements 311 in a predetermined manner. The controller 334 may change frequency, power, focal length and/or operating time to provide the desired ablating technique. The change in frequency and power may be completely automatic or may require user input. Input may come from a user interface. Control signals may get to and from the controller, the channels, and the ablating elements using wires, data buses, or other methods of transmitting power and/or control signals known to those skilled in the art. The controller 334 may also be coupled to at least one temperature sensor 336, fluid source 342, and/or a vacuum source 318 for controlling the ablating device 300. The sensors may provide feedback via a low voltage signal through an electrical coupling (not shown) to the controller 334. The controller 334 may utilize feedback, such as temperature-based feedback or electrical impedance to actively control the ablations. The controller 334 may automatically sequence through two or more different ablating techniques. The controller 334 may use other techniques depending on the tissue characteristics and the type or types of ablating elements 311 controlled. The controller 334 may contain at least one or more of the following: a temperature display 335, a timer 337, a digital readout 377, and/or lights 379. The controller 334 may also contain or connect to a remote display (not shown). Though only one controller 334 is shown, in other embodiments a plurality of control systems 334 may be used, with each controller 334 controlling at least one function of the ablation device.

In the embodiment illustrated in FIG. 5, a controller controls ablation at each cell 304 based on temperature measured by at least one temperature sensor 336. In this embodiment, the temperature sensors 336 are contained in cells 304, but the number and location of the temperature sensor 336 shown is exemplary only. The temperature sensor 336 may be located on the near surface NS of the tissue, the far surface FS, or in the interior of the tissue. The at least one temperature sensor 336 may measure the temperature of the at least one cell 304, the at least one ablating element 311 and/or the temperature at a near surface of the tissue closest to the at least one ablating element 311. The temperature can be adjusted by changing any one or more of the frequency, power, focal length and/or operating time the power is delivered to the ablating element 311. The controller 334 may be configured to maintain a tissue near surface NS temperature of 0-80 degrees C, more preferably 20-80 degrees C, and most preferably 40-80 degrees C. The controller 334 may have a multiplexer 333 coupled to a temperature sensor 336 which delivers energy to only the cells 304 having a temperature below the threshold temperature. In another embodiment, the multiplexer 333 may deliver energy to the coldest cells 304 or to a number of cells 304 which register the coolest temperatures. In some embodiments a switching matrix may be used to selectively deliver energy to the ablating elements 311. The multiplexer may be located within the controller or it may be located with the ablating elements. The multiplexer or switching matrix may be placed in other locations as well, as long as they remain in electrical communication with the ablating elements.

Ablation may be controlled in a number of different ways. For example, power may be distributed to adjacent cells 304 or to at least one pair of adjacent cells 304 such as a first and second cell 304 or a fifth and sixth cell 304. After power is distributed to these adjacent cells 304, power is distributed to another pair or pairs of adjacent cells 304 such as a third and fourth cells 304 or a seventh and eighth cells 304. The controller 334 may activate at least one pair of adjacent ablating elements 311 to form continuous lesions between the adjacent ablating elements 311. After ablation at the at least one pair of adjacent ablating elements 311, another pair of adjacent ablating elements 311 is activated to form another continuous ablation segment. In another mode of operation, the controller 334 energizes ablating elements 311 by distributing power to each cell 304 with an ablating element 311. The cells 304 may be numbered. In another mode of operation, the controller 334 energizes ablating elements 311 in every other cell 304, every third cell 304, or a limited number of cells 304, up four cells 311 at any given time. The controller 334 may activate less than 50%, even less than 30%, of the total ablation area at one time. A percentage of the total ablation area is essentially a percentage of the total number of ablating elements 311. This process continues until a continuous lesion of the desired geometry is produced.

Figure 8:
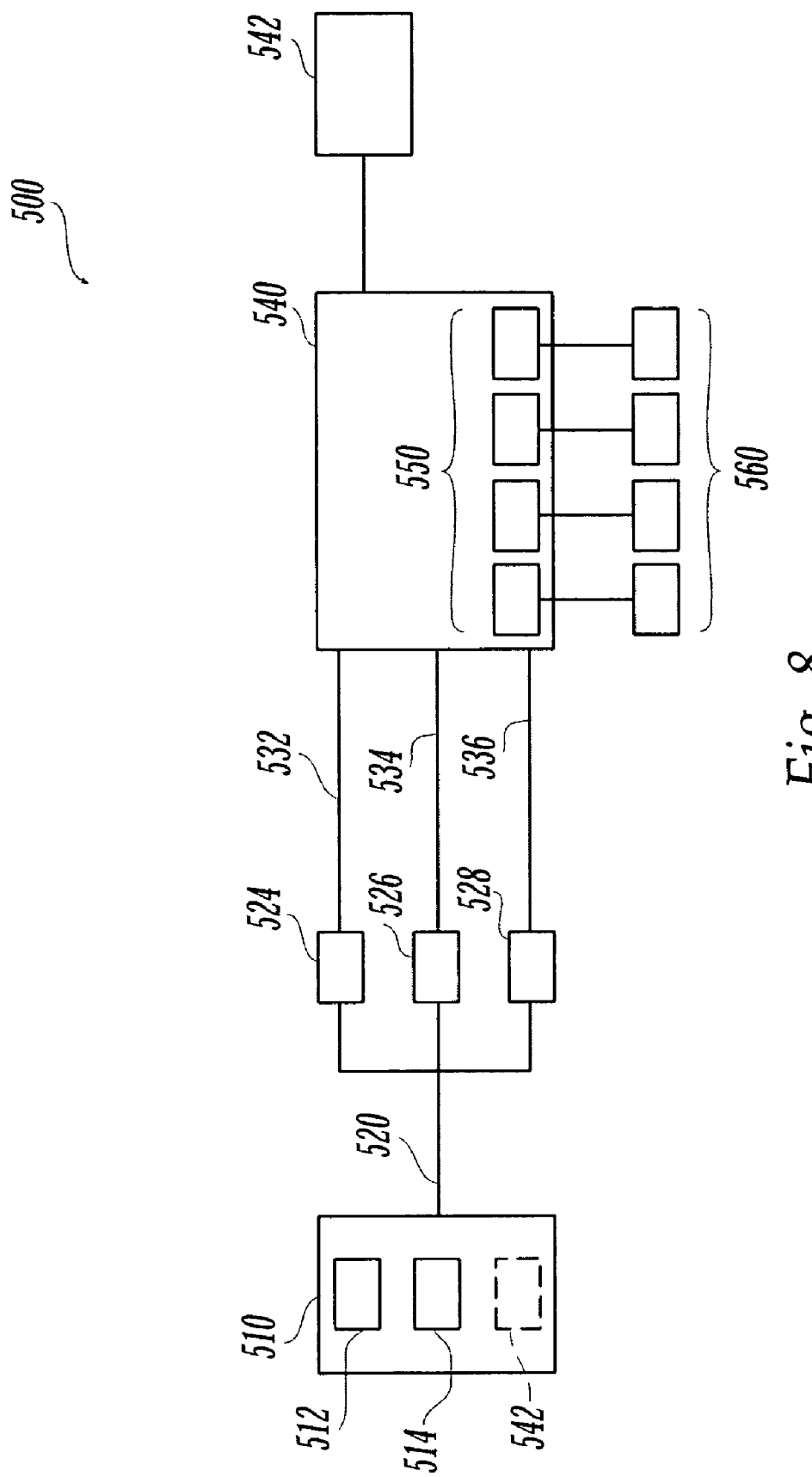
FIG. 8 illustrates an embodiment of an ablation control system controller.

FIG. 8 illustrates an embodiment of an ablation control system 500 with an ablation control system controller 510. The controller 510 controls the distribution of power from a single power source (not shown). The controller 510 produces an ablation element driving signal input 520 that connects to the inputs of a first, second, and third terminal set 524, 526, and 528. The controller may further have a driving signal generator 512 for generating an ablation driving signal input. The controller 510 may also have a power switching controller 514 for controlling the switching of the terminal sets. The quantity and location of the driving signal generator 512, power switching controller 514, and terminal sets is exemplary only, and not limited to the embodiment shown. The first, second, and third terminal sets 524, 526, 528 in the embodiment shown further connect to three independent driving signal output channels 532, 534, 536, which are connected to an input of a relay switching matrix 540. The quantity and location of the driving signal output channels are exemplary only, and not limited to what is shown. The relay switch matrix 540 contains a plurality of relay switches (not shown), with the relay switches further connecting to a plurality of ablating element attachment sites 550. The quantity and location of the ablation element attachment sites 550 is exemplary only, and not limited to what is shown. The relay switching matrix 540 may be connected to a relay switch controller 542 which controls the opening and closing of the plurality of relay switches. Although shown connected to the relay switching matrix 540, the relay switch controller 542 may be located with the ablation control system controller 510. These locations are exemplary only. The relay switch controller 542 may be in any location where it is in communication with the relay switching matrix 540 and the ablation system controller 510. A plurality of ablating elements 560 may connect to the ablating element attachment sites 550. The ablating elements 560 may contain a radiofrequency (RF) electrode, microwave transmitter, cryogenic element, laser, ultrasonic transducer, and/or any other device suitable for forming transmural lesions.

FIG. 9 illustrates an embodiment of an ablation control system 500 with four terminal sets, one of which is a bypass terminal set not shown in FIG. 8. The four terminal sets deliver power from a single power source (not shown) through three channels 532, 534, 536 (labeled as channels A, B, and C). Power is distributed from a single power source (not shown) to the ablating elements 560 (see FIG. 8) as if three power sources were being used instead of one by fast, cyclical switching of transmission of the ablation element driving signal input 520 among the three channels. An electromechanical dual-pole dual-throw (DPDT) switch 570, shown schematically as two single-pole dual-throw (SPDT) switches SW 1/2 and SW 2/2, acts as the fourth terminal set 522, which is the bypass terminal set. The first through third terminal sets 524, 526, and 528 are shown schematically as three single-pole single-throw (SPST) switches SW 2, SW 3, and SW 4, which provide three possible "on" switching positions for the three channels 532, 534, 536 when the bypass terminal set 522 (i.e., DPDT switch 570) is turned off. Alternatively, the three switches (may be referred to as first switches herein) may be replaced by in a single-pole triple-throw (SPTT) fast solid state switch 580 as shown in FIG. 9A, which also provides three possible "on" switching positions between the channel source 520 and the three channels 532, 534, 536, respectively, in a different embodiment. In this disclosure, a switch is broadly defined as a device or a component that allows the opening and closing of an electrical circuit or electrical connection (i.e., an on/off connection). Although the SPTT switch 580 is embodied in a single switch device, it is considered to comprise three switches because it allows the opening and closing of three electrical connections between the channel source and the three channels (i.e., it has three possible "on" switching positions between the channel source and the three channels, respectively).

A controller 510 (see FIG. 8) produces an ablating element driving signal input 520. In certain embodiments, switching among all channels may occur even if an ablating element 560 is not energized on a particular channel. Thus, switching among channels may occur independently of individual ablating elements. Switching among channels may also occur if all ablating elements on a given channel are inactive. In other embodiments, switching among channels may occur even if one or more channels fail, allowing for continued distribution of power to the remaining operational channels. In other embodiments, switching among channels may be controlled based on whether or not elements of a particular channel are required to be energized during a switching cycle.

The SPTT fast solid state switch 580 of FIG. 9A or the group of three switches 524, 526, 528 of FIG. 9 selectively connect the channel source 520 to one of the first, second, and third driving signal output channels 532, 534, and 536. The SPTT fast solid state switch 580 switches at a switching cycle speed fast enough to distribute power among driving signal output channels 532, 534, and 536 so that the rate of tissue ablation decreases insignificantly. The time it takes the rate of tissue ablation to decrease insignificantly is known as the thermal time constant. The rate of tissue ablation desirably remains substantially constant, for instance, by a change of at most 10%, more preferably by a change of at most 5%, and most preferably by a change of nearly 0%. Although the change in rate of tissue ablation is preferably 5% or less, other changes in the rate of tissue ablation may be used to calculate a thermal time constant in other embodiments. For example, a rate of 6% could be used. In one specific ablation example, a 5% decrease in ablation rate converts into a change in temperature of about 0.07 degrees centigrade. Thus, in this example the thermal time constant is the time it takes ablated tissue temperature to decrease by about 0.07 degrees centigrade. For typical tissue of typical thickness, the thermal time constant is approximately 0.1 seconds. The switching cycle of the switches must be at least as fast as the thermal time constant. One switching cycle is defined as the time it takes to switch power from one channel to the next one time for all channels. Accordingly, if only one power source were used, the switch would switch that source to all channels once each cycle, and completes each cycle within one thermal time constant. With a thermal time constant of approximately 0.1 seconds this equates to a switching cycle period of about 0.1 seconds or less if one power source supplied power to all channels. In the embodiment shown, with one power source supplying power to three channels, this means that power is switched from one channel to the next approximately every 0.03 seconds representing ⅓ duty cycle over the switching period. More generally, if there were one power source supplying power to M channels in an embodiment with a thermal time constant of T seconds, power would switch from one channel to the next in T/M seconds.

In the embodiment shown, the DPDT switch 570 allows the SPTT fast solid-state switch 580 to be bypassed entirely to avoid signal distortion during the load calibration stage, or to provide another mode of operation that does not require fast switching for distributing power from one power source to multiple ablation elements. If an AC power source is used, the AC power defines a modulated first driving signal input envelope. The switching action produces pulse trains on driving signal output channels. The driving signal output channel signals contain modulated driving signal output envelopes which contain pulse train signals defined by the first envelope. Although the SPTT fast solid state switch 580 preferably distributes power at a cycle speed of 0.1 seconds, and switches between two of the three channels approximately every 0.03 seconds, it may distribute power at slower speeds.

Figure 10:
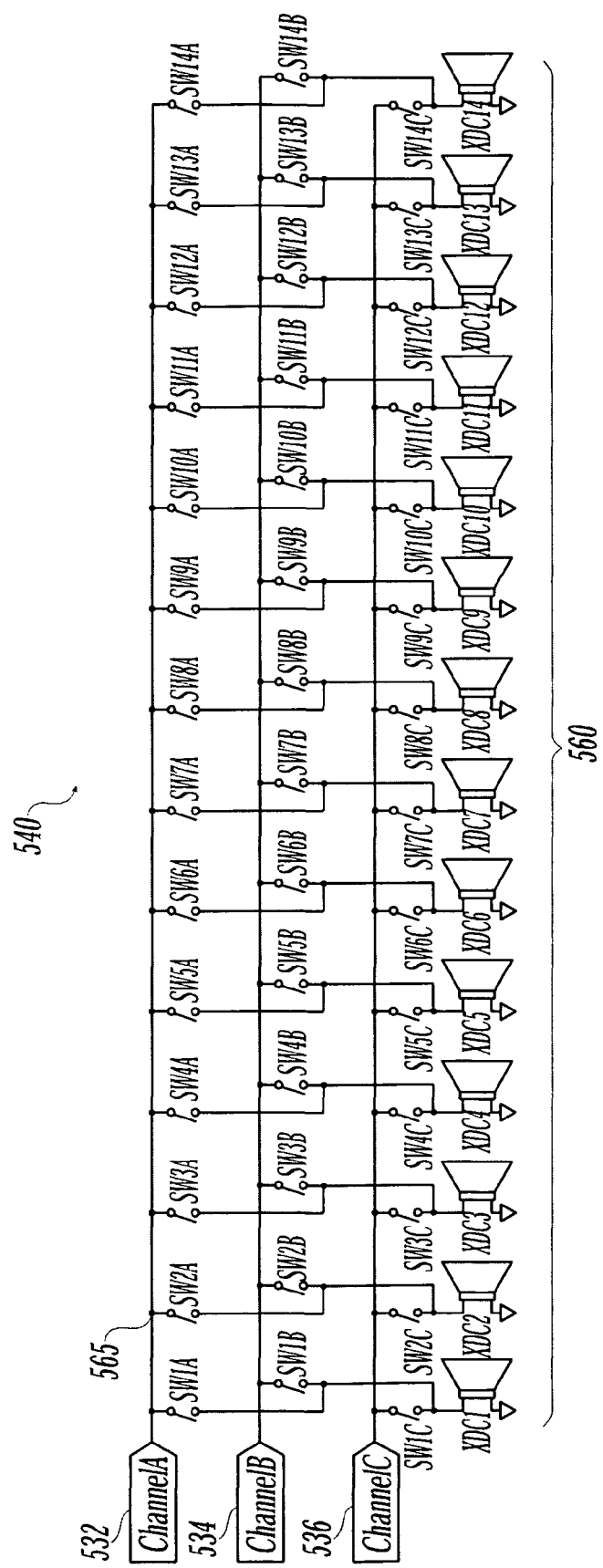
FIG. 10 illustrates an embodiment of an ablation control system relay switch matrix.

FIG. 10 illustrates an embodiment of an ablation control system with the ablating elements (or other power receiving members) connecting to a relay switch matrix 540. In the embodiment shown, a 3×14 relay switch matrix 540 receives input from three driving signal output channels 532, 534, and 536 (labeled as channels A, B, and C) which receive power from three power sources (not shown). The speed of the switches in the matrix 540 is independent of the power switching speed among channels. The number of channels is exemplary only, and not limited to what is shown. Three driving signal output channels 532, 534, and 536 connect to 14 ablating elements 560 via 42 electromechanical relays 565 (may be referred to as second switches herein) in the relay switch matrix 540. The ablating elements 560 are labeled XDC 1 through 14. The electromechanical relays 565 connect the ablating elements 560 to the driving signal output channels 532, 534, and 536. Up to three of the 14 ablating elements 560 may be powered at a given time, with no more than one driving signal output channel delivering power to an ablating element 560 at a time. In this embodiment, the switching speed of the second switches 565 is substantially lower than the switching speed of the first switches 524, 526, 528 (or the SPTT switch 580). For example, the switching speed of the second switches may be at least one order of magnitude lower. The second switches 565 may be electromechanical relays that need not be as durable as solid state switches for high speed switching required of the first switches. At high speed switching with a switching period on the order of about 0.1 seconds, the first switches are substantially more durable than the second switches, and can last much longer without failure than the second switches (e.g., at least 10 times, more preferably at least 100 times more durable). The second switches direct the power input signal from the first switches to one subset of the ablation elements at a time (e.g., about 10-40 seconds at a time) before switching to another subset of the ablation elements. In the embodiment shown in FIG. 10, there are fourteen ablation elements 560 and each subset has three ablation elements 560. During that time, the power input signal is switched among the ablation elements in the subset of the ablation elements one at a time according to the switching speed of the first switches. Subsequently, different subsets of the ablation elements are selected to receive the power input signal or driving signal input by operation of the second switches. In one example, the ablation elements are arranged in a closed loop, and each subset of the ablation elements form a group of neighboring ablation elements within a portion of the closed loop.

Figure 11:
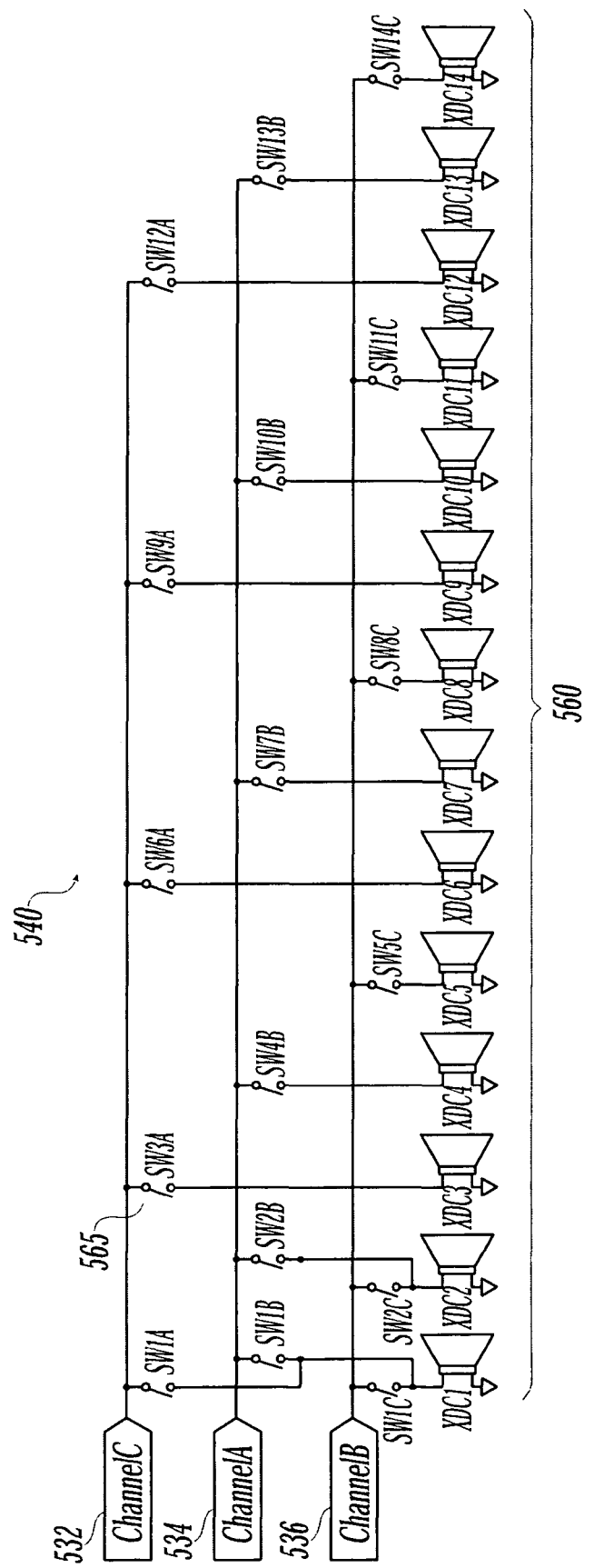
FIG. 11 illustrates another embodiment of an ablation control system relay switch matrix.

FIG. 11 illustrates another embodiment of an ablation control system 500 with the ablating elements connecting to a relay switch matrix 540. The embodiment shown has 14 ablating elements 560. Three driving signal output channels 532, 534, and 536 (labeled as channels A, B, and C) deliver power to the ablating elements. Channel A drives ablating elements 1, 2, 4, 7, 10, and 13. Channel B drives ablating elements 1, 2, 5, 8, 11, and 14. Channel C drives ablating elements 1, 3, 6, 9, and 12. The speed of the switches in the matrix 540 is independent of the power switching speed among channels. In this embodiment, rather than employing a 3×14 switching matrix 540 with one relay switch 565 per ablating element 560 for each channel, only 17 relay switches 565 (may be referred to as second switches herein) are required. In other embodiments with N ablating elements 560 and M driving signal output channels, the number of relay switches 565 is reduced from N times M (N*M) to N plus M (N+M). This reduction in the number of relay switches 565 reduces the cost, complexity, part count, and physical volume of the switching matrix 512. The reduction in physical volume also allows the switching matrix 540 to be moved closer to the ablating elements 560, which reduces the power dissipated in the cables connecting the switching matrix 540 outputs to the ablating elements 560.

One method of ablating tissue is now described. Although the treatments described use ultrasonic transducers 406, each of the treatments described may be used by itself and/or in combination with any other treatment. The combination of transducer size, type, power, frequency, ablating time, and focal length may all be varied to produce the desired delivery of energy to the tissue. The preferred embodiment may be adjusted by simply adjusting one or more of the characteristics, and thus these parameters may be changed without departing from various aspects of the invention. In the method described, the ablating device 400 is operated during two different time periods while varying at least one characteristic of the ablating device 400 such as the frequency, power, position of the focus relative to the tissue, and/or ablating time. For example, the ablating device 400 may be operated at varying frequencies over time to ablate tissue in a controlled manner. Specifically, the ablating device 400 is preferably operated to create a transmural lesion by controlling the delivery of energy to the tissue. Although it is preferred to vary the frequency when ablating the tissue, the device may be operated at a single frequency.

First, the transducer 406 is activated in short bursts at a frequency of 2-7 MHz, preferably about 3.5 MHz. For example, the transducer 406 may be activated for 0.01-1.0 second and preferably about 0.4 seconds. The transducer may be activated at a power of 80-140 watts, preferably about 110 watts. A few exemplary locations of where power may be measured from include the output of the power source, the input to the ablating element, and/or the output of the ablating element. The transducer 406 is inactive for about 2-90 seconds, more preferably 5-80 seconds, and most preferably about 45 seconds between activations. In this manner, a controlled amount of accumulated energy can be delivered to the tissue in short bursts to heat tissue at and near the focus and minimizes the impact of blood cooling at the far surface FS. Ablation at this frequency may continue until a controlled amount of energy is delivered such as about 0.5-3 kilojoules. Ablation at this frequency in relatively short bursts produces localized heating at the focus. At the first frequency, energy is not absorbed as quickly in tissue as it is at higher frequencies so that heating at the focus is not significantly affected by absorption of energy in the tissue.

Following ablation at the first frequency, the transducer 406 is operated for longer periods of time, preferably about 1-4 seconds and more preferably about 2 seconds, to ablate tissue between the focus and the transducer 406. The frequency during this ablation is also 2-14 MHz, more preferably 3-7 MHz and preferably about 6 MHz. The transducer 406 is operated for 0.7-4 seconds at a power of 20-60 watts, preferably about 40 watts. The transducer 406 is inactive for at least 3 seconds, more preferably at least 5 seconds, and most preferably about 10 seconds activations. In this manner, a controlled amount of energy can be delivered to heat tissue between the focus and the transducer. Ablation at this frequency may continue until a controlled amount of total energy is delivered such as about 750 joules.

Next, the transducer is activated at a higher frequency to heat and ablate the near surface NS. The transducer is preferably operated at a frequency of at least 6 MHz, more preferably at least 10 MHz, and most preferably about 16 MHz. The transducer 406 is operated at lower power than the treatment methods above since the ultrasonic energy is rapidly absorbed by the tissue at these frequencies so that the near surface NS is heated quickly. In a preferred method, the transducer is operated at 2-10 watts and more preferably about 5 watts. The transducer 406 is preferably operated until the near surface NS temperature reaches 70-85 degrees C.

Other embodiments of the switching apparatus and methods described can be used in the present invention. For example, the apparatus may be used for pacing the heart by delivering current through at least one electrode at levels sufficient to stimulate heart contractions. Still other examples of devices and methods are disclosed in U.S. Pat. No. 6,719,755 which is herein expressly incorporated by reference. Various alternatives, substitutions and modifications for each of the embodiments and methods of the invention may be made without departing from the scope thereof, which is defined by the following claims.

What is claimed:

1. An ablation element power switching apparatus comprising:
    a plurality of first switches having an input end to receive a power input signal, each first switch having an output end;
    a plurality of second switches, each second switch having an input end coupled to the output end of at least one first switch, each second switch having an output end;
    a bypass switch having an input end to receive the power input signal and an output end coupled to the second switches,
    wherein in an on position, the bypass switch bypasses the first switches to transmit the power input signal to the second switches;
    a plurality of power receiving members, each power receiving member having an input end coupled to the output end of at least one second switch; and
    a controller selectively turning on the first switches one at a time in a cyclical manner according to a first switching rate to transmit the power input signal, the controller selectively turning on the second switches one subset of the second switches at a time according to a second switch rate to transmit the power input signal from the first switches to a subset of power receiving members one power receiving member at a time within the subset of power receiving members according to the first switching rate,
    wherein the first switching rate is substantially faster than the second switching rate, and
    further wherein each fist switch is configured to transmit the power input signal independendent of the switching position of the other of the plurality of first switches.

2. The power switching apparatus of claim 1, wherein the first switching rate is faster than the second switching rate by at least one order of magnitude.

3. The power switching apparatus of claim 1, wherein each subset of the second switches are equal in number to the first switches and equal in number to each subset of the power receiving members.

4. The power switching apparatus of claim 1, wherein the first switches are solid state switches.

5. The power switching apparatus of claim 1, wherein the second switches are electromechanical relays.

6. The power switching apparatus of claim 1, wherein the power receiving members are arranged in a closed loop, and wherein each subset of the power receiving members form a group of neighboring power receiving members within a portion of the closed loop.

7. The power switching apparatus of claim 1, wherein the first switching rate is such that for each first switching cycle, a first switching period is at most about 0.1 seconds and the first switches are each turned on once for about the same duty cycle over the first switching period.

8. The power switching apparatus of claim 1, comprising three first switches.

9. The power switching apparatus of claim 1, comprising N power receiving members, M first switches, and at most M×N second switches.

10. The power switching apparatus of claim 1, comprising N power receiving members, M first switches, and at most M+N second switches.

11. The power switching apparatus of claim 1, wherein when the bypass switch is in the on position, the controller selectively turns on the second switches to transmit the power input signal to the power receiving members one at a time in a cyclical manner.

12. A power switching apparatus comprising:
a plurality of first switches having an input end to receive a power input signal, each first switch having an output end;
a plurality of second switches, each second switch having an input end coupled to the ouput end of at least one first switch, each second switch having an output end;
a bypass switch having an input end coupled to the power input signal and An output end coupled to the second switches,
wherein in an on position, the bypass switch bypasses the first switches to Transmit the power input signal to the second switches;
a plurality of ablation members, each ablation member having an input end coupled to the output end of at least one second switch; and
a controller selectively turning on the first switches one at a time in a cyclical manner according to a first switching rate to transmit the power input signal, the controller selectively turning on the second switches one subset of the second switches at a time according to a second switch rate to transmit the power input signal from the first switches to a subset of ablation members one ablation member at a time within the subset of ablation members according to the first switching rate,
wherein the first switching rate is such that for each first switching cycle, a first switching period is at most about T seconds during which each first switch is turned on once, and that a rate of tissue ablation of the tissue to be ablated by each ablation member remains substantially constant during the first switching period,
further wherein each first switch is configured to transmit the power input signal independent of the switching position of the other of the plurality of first switches.

13. The power switching apparatus of claim 12, wherein the first switching rate is such that the rate of tissue ablation of the tissue to be ablated by each ablation member changes at most by about 5% during the first switching period.

14. The power switching apparatus of claim 12, wherein the first switching period is at most about 0.1 seconds.

15. The power switching apparatus of claim 12, wherein each subset of the second switches are equal in number to the first switches and equal in number to each subset of the ablation members.

16. The power switching apparatus of claim 12, wherein for each first switching cycle, each first switch is turned on once for about the same duty cycle over the first switching period.

17. The power switching apparatus of claim 12, wherein the first switches are solid state switches.

18. The power switching apparatus of claim 12, wherein the ablation members are arranged in a closed loop, and wherein each subset of the ablation members form a group of neighboring ablation members within a portion of the closed loop.

* * * * *